United States Patent [19]
Singh et al.

[11] Patent Number: 6,166,220
[45] Date of Patent: Dec. 26, 2000

[54] ETHYLENICALLY UNSATURATED IMIDAZIDOLIDINONE MONOMERS

[75] Inventors: Balwant Singh, Stamford; Roland Ralph DiLeone, Rowayton; Laurence Wu-Kwang Chang, New Haven, all of Conn.

[73] Assignee: Cytec Technology Corp., Wilmington, Del.

[21] Appl. No.: 08/881,623

[22] Filed: Jun. 24, 1997

Related U.S. Application Data

[60] Provisional application No. 60/020,333, Jun. 24, 1996, and provisional application No. 60/038,896, Feb. 21, 1997.

[51] Int. Cl.[7] .................. C07D 233/36; C07D 233/38; C07D 233/32
[52] U.S. Cl. .................. 548/313.4; 548/324.1; 548/324.5
[58] Field of Search .................. 548/313.4

[56] References Cited

U.S. PATENT DOCUMENTS

| | | | |
|---|---|---|---|
| 2,727,016 | 12/1955 | Hankins et al. | 260/77.5 |
| 2,727,019 | 12/1955 | Melamed | 260/79.7 |
| 2,881,171 | 4/1959 | Hankins | 260/256.4 |
| 2,980,652 | 4/1961 | Melamed et al. | 260/77.5 |
| 3,194,792 | 7/1965 | Emmons et al. | 260/77.5 |
| 3,356,653 | 12/1967 | Sekmakas | 260/78.5 |
| 3,356,654 | 12/1967 | Sekmakas | 260/78.5 |
| 3,369,008 | 2/1968 | Hurwitz | 260/80.72 |
| 3,509,085 | 4/1970 | Sekmakas | 260/29.6 |
| 4,104,220 | 8/1978 | Sims | 260/29.6 R |
| 4,111,877 | 9/1978 | Dixon et al. | 260/29.6 R |
| 4,219,454 | 8/1980 | Iacoviello et al. | 260/29.6 T |
| 4,314,067 | 2/1982 | Herman et al. | 548/320 |
| 4,319,032 | 3/1982 | Sandri et al. | 548/320 |
| 4,426,503 | 1/1984 | Sandri et al. | 526/263 |
| 4,577,031 | 3/1986 | Iovine et al. | 548/319 |
| 4,596,850 | 6/1986 | Iovine et al. | 524/548 |
| 4,599,417 | 7/1986 | Sekmakas et al. | 544/316 |
| 4,617,364 | 10/1986 | Sekmakas et al. | 526/263 |
| 4,622,374 | 11/1986 | Iovine et al. | 526/263 |
| 4,632,957 | 12/1986 | Welsh et al. | 524/548 |
| 4,730,045 | 3/1988 | Sekmakas et al. | 544/318 |
| 4,766,221 | 8/1988 | Floyd | 548/320 |
| 4,770,668 | 9/1988 | Skoultchi et al. | 8/181 |
| 4,777,265 | 10/1988 | Merger et al. | 548/320 |
| 4,783,539 | 11/1988 | Abboud et al. | 548/320 |
| 4,845,233 | 7/1989 | Higuchi et al. | 511/398 X |
| 4,883,873 | 11/1989 | Abboud et al. | 544/316 |
| 5,210,199 | 5/1993 | Grosius et al. | 548/324.1 |
| 5,235,016 | 8/1993 | Vafa et al. | 526/304 |
| 5,496,907 | 3/1996 | Dochniak | 528/73 |
| 5,498,723 | 3/1996 | Riondel et al. | 548/324.1 |
| 5,567,826 | 10/1996 | Knebel et al. | 548/324.1 |
| 5,610,313 | 3/1997 | Riondel et al. | 548/324.1 |

FOREIGN PATENT DOCUMENTS

| | | |
|---|---|---|
| 240370 | 10/1987 | European Pat. Off. . |
| 0629672 A2 | 12/1994 | European Pat. Off. . |
| 0629672 A3 | 12/1994 | European Pat. Off. . |
| WO91/12243 | 8/1991 | WIPO . |

OTHER PUBLICATIONS

International Search Report dated Oct. 31, 1997 for PCT/US97/10951.

S.M. Kambanis and G. Chip, "Polymer and Paint Properties Affecting Wet Adhesion," *Journal of Coatings Technology*, vol. 53, No. 682 (Nov. 1981), pp 57–64.

*Primary Examiner*—Robert W. Ramsuer
*Attorney, Agent, or Firm*—Valerie T. Didamo

[57] ABSTRACT

Classes of urea functional compounds and compositions containing the same are disclosed which are particularly suitable for use as a wet adhesion promoters in coatings, especially in aqueous emulsion systems used to make latex paints. Compositions containing the same, as well as additional uses thereof are also disclosed.

20 Claims, No Drawings

ETHYLENICALLY UNSATURATED IMIDAZIDOLIDINONE MONOMERS

This application claims the benefit of U.S. Provisional application Ser. Nos. 60/020,333 and 60/038,896 filed Jun. 24, 1996 and Feb. 21, 1997, respectively, both of which are incorporated by reference herein as if fully set forth.

BACKGROUND OF THE INVENTION

1. Field of the Invention

This invention relates to ethylenically unsaturated polymerizable monomers which are particularly suitable for use as wet adhesion promoters. More specifically, the polymerizable monomers of the present invention are useful to promote adhesion in polymers and copolymers, and especially in aqueous emulsion copolymer latices which are used to prepare latex paints.

2. Description of Related Art

The term "wet adhesion" is used in the paint industry to describe the ability of a paint to retain its adhesive bond to a substrate under wet or high humidity conditions. While oil-based systems are known to retain their adhesive properties under wet or humid conditions, the tendency of many water based coatings (i.e., latices) to lose their adhesive properties when wet has limited the usefulness of such coatings. The wet adhesion deficiency of latex paints also makes surfaces painted with such paints less scrub resistant than those surfaces painted with organic solvent based paints. See S. M. Kabanis and G. Chip, "Polymer and Paint Properties Affecting Wet Adhesion," *Journal of Coatings Technology*, 53(682), 57–64 (November 1981).

Since the use of water-based emulsion polymer systems as protective and decorative coatings for many types of surfaces has become widespread, such systems being used by individuals in homes and in industry, there is a great need for improved wet adhesion of such systems. In recent years, the art has recognized the problem of loss of adhesive properties in latex paints and a variety of additives to latex systems to improve wet adhesion have been proposed. Incorporation of amine, amide and acetoacetate functionalities into latex polymers has been reported to improve the wet adhesion properties of latex paints. A number of publications also describe the use of urea and ureido-functional monomers for such purpose. See, for example, U.S. Pat. No. 2,72,7016, U.S. Pat. No. 2,727,019, U.S. Pat. No. 2,881,171, U.S. Pat. No. 2,980,652, U.S. Pat. No. 3,194,792, U.S. Pat. No. 3,356,654, U.S. Pat. No. 3,369,008, U.S. Pat. No. 3,509,085, U.S. Pat. No. 4,104,220, U.S. Pat. No. 4,111,877, U.S. Pat. No. 4,219,454, U.S. Pat. No. 4,314,067, U.S. Pat. No. 4,319,032, U.S. Pat. No. 4,426,503, U.S. Pat. No. 4,596,850, U.S. Pat. No. 4,599,417, U.S. Pat. No. 4,617,364, U.S. Pat. No. 4,622,374, U.S. Pat. No. 4,730,045, U.S. Pat. No. 4,766,221, U.S. Pat. No. 4,770,668, U.S. Pat. No. 4,777,265, U.S. Pat. No. 4,783,539, U.S. Pat. No. 4,883,873, U.S. Pat. No. 5,210,199, U.S. Pat. No. 5,498,723, U.S. Pat. No. 5,567,826, U.S. Pat. No. 5,610,313 and WO91/12243, all of which are incorporated by reference herein for all purposes as if fully set forth.

A number of these known urea/ureido functional monomers, however, have provided unsatisfactory wet adhesion results. Many may also be very expensive and their inclusion into latex polymers results in a substantial increase in the cost of the vinyl, vinyl-acrylic and all-acrylic polymers used in latex-based paints.

It has now been discovered that excellent wet adhesion properties can be imparted into aqueous emulsion systems used to make latex paints by incorporating into the monomer system, from which the polymer is produced, a new class of urea/ureido functional polymerizable monomers including cyclic urea moieties derived from alkyleneureas, hydroxyalkylalkyleneureas, aminoalkylalkyleneureas and their Diels-Alder adducts with 1,3-dienes.

Latex-containing surface coatings and coating compositions having superior wet adhesion properties may therefore be produced by including in the monomer system one or a mixture of the monomers of the present invention. In particular the monomers of this invention have been found to be especially useful in water-based latex-containing paints.

SUMMARY OF THE INVENTION

As indicated above, the present invention is directed to novel polymerizable monomers for use in aqueous emulsions. The compounds of the present invention may be represented by the following general Formula (1)

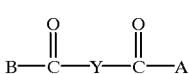

wherein Y is

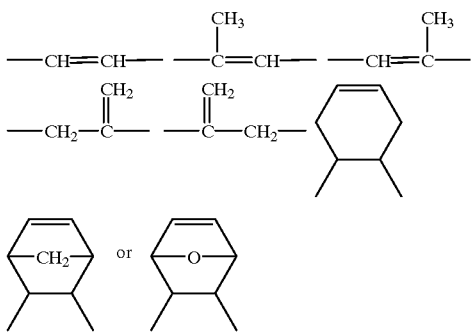

wherein A is

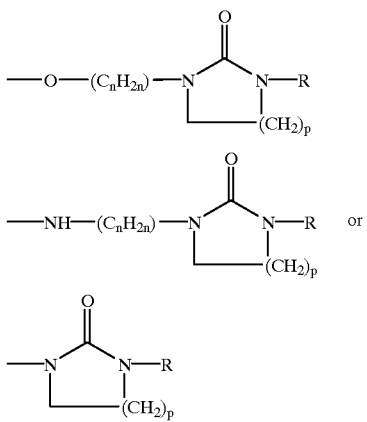

wherein B is

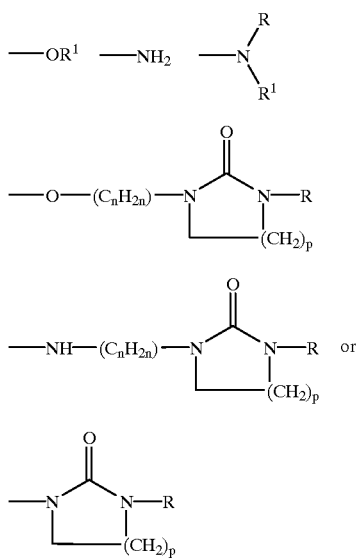

wherein each R is individually

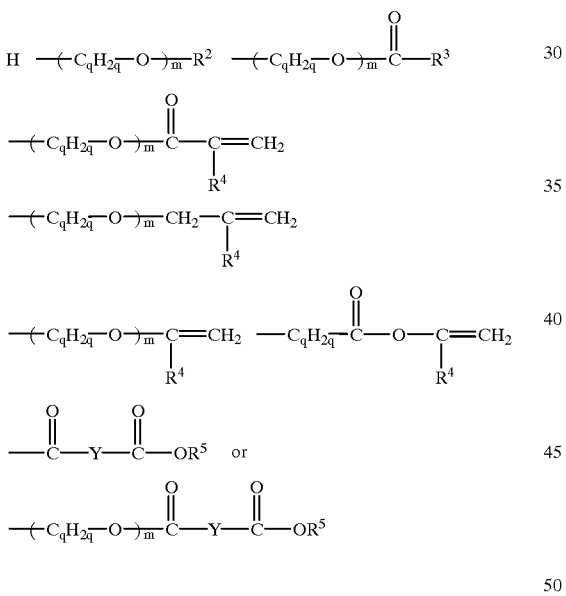

wherein each $R^1$ is individually an aliphatic, alicyclic or aromatic moiety having up to 24 carbon atoms

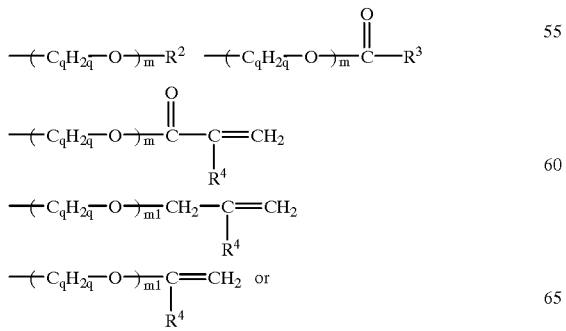

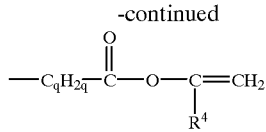

wherein each $R^2$ is individually hydrogen or an aliphatic, alicyclic or aromatic moiety having up to 24 carbon atoms wherein each $R^3$ is individually an aliphatic, alicyclic or aromatic moiety having up to 24 carbon atoms wherein each $R^4$ is individually hydrogen or a methyl group wherein each $R^5$ is individually hydrogen or an aliphatic, alicyclic or aromatic moiety having up to 24 carbon atoms wherein m is an integer of from 1 to 4 wherein m1 is 0 or an integer of from 1 to 4 wherein n is an integer of from 1 to 8 wherein p is 1 or 2, and wherein q is an integer of from 1 to 4, with the provisos that:

(1) when A is

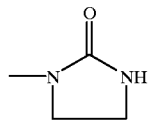

and B is —$OR^1$, then $R^1$ is

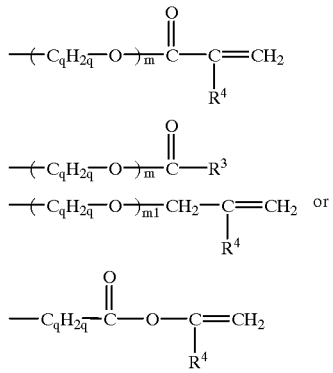

(2) when A is

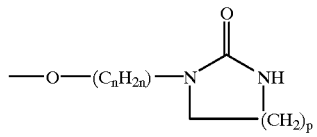

and B is —$OR^1$, then $R^1$ is an aliphatic, alicyclic or aromatic moiety having up to 24 carbon atoms

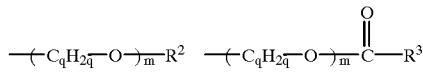

-continued

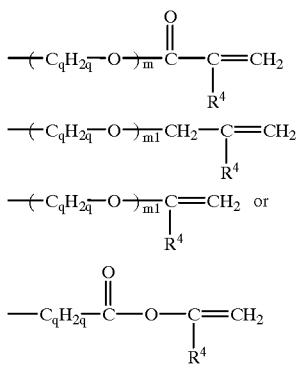

wherein $R^2$ is an aliphatic, alicyclic or aromatic moiety having up to 24 carbon atoms;
and (3) when A is

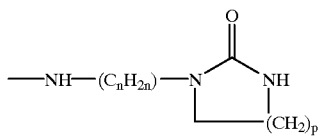

and B is —$OR^1$, then $R^1$ is

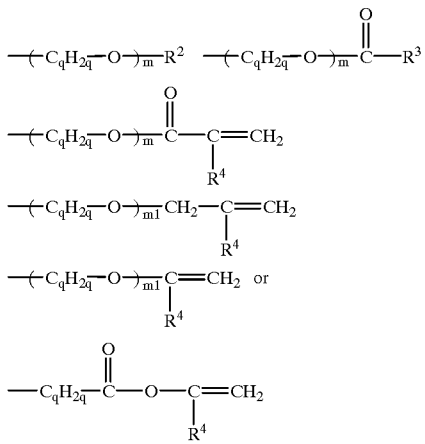

wherein $R^2$ is an aliphatic, alicyclic or aromatic moiety having up to 24 carbon atoms.

Both the cis- and trans-stereoisomers of the above compounds, where appropriate (e.g., maleic and fumaric), are included within the above definition and the scope of the invention. It is also within the scope of the invention to use mixtures of the novel compounds of Formula (1) in aqueous emulsion polymer systems.

The novel polymerizable monomers of the present invention are capable of polymerization through their double bond(s). Thus, the novel monomers of the invention are useful as components of monomer systems, particularly free-radically polymerizable monomer systems, especially those used in forming aqueous emulsion polymers for paint, coatings and adhesives.

Accordingly, the invention includes polymers prepared from ethylenically unsaturated monomers, at least one of which is a compound of the Formula (I), and compositions comprising such polymers, especially acrylic, vinyl, vinyl-acrylic, and styrene-acrylic latex paints comprising polymers made from the novel polymerizable monomers of this invention.

In addition, the present invention provides a method of enhancing the adhesion/wet adhesion of aqueous and organic solvent-borne polymer systems by incorporating the novel functional monomers of the present invention in the precursor monomer mixtures. More specifically, the present invention provides a method for enhancing the wet adhesion properties of a polymer derived from the addition polymerization of an ethylenically unsaturated monomer system, by incorporating into the ethylenically unsaturated monomer system, prior to polymerization, one or more compounds of the formula (I).

The present invention further provides a method for enhancing the wet adhesion properties of a polymer system, such as latex polymer system, by mixing into such polymer system a polymer of one or more ethylenically unsaturated monomers, wherein at least one of the ethylenically unsaturated monomers is a compound of the formula (I).

These and other features and advantages of the present invention will be more readily understood by those skilled in the relevant art from a reading of the following detailed description.

DETAILED DESCRIPTION OF THE PREFERRED EMBODIMENTS

As indicated above, the present invention relates most broadly to functional monomers of the general Formula (I) shown above, which contain one or more cyclic urea functionalities.

Preparation of the Novel Functional Monomers

The functional monomers of the Formula (I) indicated above may be derived from such known compounds such as maleic anhydride, citraconic anhydride, itaconic anhydride, tetrahydrophthalic anhydride, endo/exo-norbornene dicarboxylic anhydride, endo/exo-3,6-epoxy-1,2,3,4-tetrahydrophthalic anhydride, and fumaric acid, as well as the corresponding amic acids, monoesters, diesters, monoamides, diamides and acid halogenates thereof.

The preferred process utilizes the diesters and diamides of maleic, fumaric, citraconic, itaconic, tetrahydrophthalic, nadic or 3,6-epoxytetrahydrophthalic acids, which can be reacted with the appropriate cyclic alkylene ureas, hydroxyalkylalkyleneureas or aminoalkylalkyleneureas in the presence of transesterification/amidation catalysts. Examples of suitable transesterification/amidation catalysts include the titanates such as tetra-i-propyltitanate (TYZOR® TPT) (titanium (IV) isoproxide) tetrabutyltitanate (TYZOR® TBT) (titanium (IV) butoxide), alkali and alkaline earth salts of β-ketoesters and β-diketones such as calcium and magnesium salts of acetoacetic acid, alkoxides and oxides of alkali and alkaline earth metals such as sodium, potassium, calcium and magnesium, tertiary amines and strong protonic acids such as $H_2SO_4$, HCl and p-toluene sulfonic acid, which may optionally be supported on inert supports, and transition metal salts such as zinc, nickel, copper or cobalt acetate, of which zinc acetate is preferred. The reaction is preferably carried out in the temperature range of 110° C.–150° C. in the presence of tetra-i-propyltitanate (TYZOR® TPT) (titanium (IV) ispropoxide) as the catalyst, with the removal of volatile alcohols.

The reaction may optionally be carried out in the presence of other comonomers such as methyl methacrylate, methacrylic acid, styrene and mixtures thereof. If these optional comonomers are esters or acids, they may enter into the above-described reaction. Their primary function, however, is to allow the final product to exist in solution form.

To prevent polymerization of the reactants and/or the product, low levels of radical inhibitors may be used. Examples of suitable inhibitors include hydroquinone, the methyl ether of hydroquinone, di-tert-butyl catechol, di-tert-butyl phenol, phenothiazene, etc. The total inhibitor concentration is typically in the range from about 100 to 2000 ppm. The preferred range of radical inhibitor is from about 200 to 250 ppm. When a radical inhibitors is used, the preferred inhibitors are methyl ether of hydroquinone and hydroquinone.

Suitable hydroxyalkylalkyleneureas and aminoalkylalkyleneureas include hydroxyethylethyleneurea, hydroxyethylpropyleneurea, aminoethylethyleneurea and aminoethylpropyleneurea. Suitable alkylene ureas include ethylene urea and propylene urea. The use of the hydroxy compounds is preferred since the amino compounds may produce by-products, for example, via Michael addition of the activated unsaturation of the diacid starting component.

A solvent is not necessary for the reaction, but if desired, nonreactive inert solvents may be employed to lower the viscosity of the reaction mixture. Examples of suitable non-reactive solvents include acetonitrile, acetone, methyl ethyl ketone, dioxane, tetrahydrofuran, ethylene glycol dimethyl ether, dimethyl formamide, dimethyl acetamide, dimethyl sulfoxide, and aromatic hydrocarbons such as toluene and xylene, and the like. When solvents are utilized, the aromatic hydrocarbons such as toluene and xylene are preferred.

Typically, a mixture of cis and trans stereoisomers, mono and bis urea/ureido derivatives, oligomeric condensation products and unreacted starting components will be obtained. Depending on reaction conditions and catalysts employed, the mixture can be adjusted in various directions as desired, for example, to result in higher bis derivative. All combinations containing ethylenic unsaturation and cyclic urea/ureido groups are active in promoting wet adhesion properties.

Although less preferred, the bis derivatives may also be prepared by reacting the cyclic urea with the appropriate anhydride followed by treatment with thionyl chloride and subsequent reaction with additional cyclic urea. Another less preferred method is react the acyl halide of the diacid, such as fumaryl chloride, with the desired cyclic urea compound.

The acryloyl, methacryloyl, allyl, methallyl and vinyl derivatives may be prepared by reacting the appropriate unsaturated alcohol or amines either concurrently or consecutively under conditions described above. For example, an unsaturated alcohol or amine (or ester or amide thereof) can be reacted concurrently with the cyclic urea and acid diester/diamide in the presence of the transesterification/transamidation catalyst. Alternatively, the unsaturated alcohol or amine can be post reacted in the presence of a transesterficiation/transamidation catalyst. Again, the use of hydroxyl and ester compounds is preferred of amines to minimize by-products.

Examples of suitable acrylic compounds include hydroxyalkyl acrylates and methacrylates such as 2-hydroxyethyl acrylate, 2-hydroxyethyl methacrylate, 2-hydroxypropyl acrylate, 2-hydroxypropyl methacrylate, and ethoxylated and propoxylated acrylic and methacrylic acid.

Examples of suitable allylic alcohols and amines include allyl alcohol, methallyl alcohol, allylamine, methallylamine, diallylamine and dimethallylamine.

Examples of suitable vinyl alcohols include ethylene glycol monovinyl ether, propylene glycol monovinyl ether, polyethylene glycol monovinyl ether and the like. Examples of suitable vinyl ester alcohols include vinyl esters of lactic acid and 3-hydroxypropionic acid.

The trans isomers of the monomers of this invention can also be prepared by isomerizing the corresponding cis isomers by heating in the presence of catalysts including, for example, hydrochloric acid, sulfuric acid, aluminum chloride and pyridine, preferably in a polar organic solvent such as acetonitrile, 1,2-dimethoxyethane, and the like.

Specific Preferred Embodiments

In a particularly preferred embodiment, the monomers of the present invention are prepared by reacting:

(1) an unsaturated dicarboxylic acid diester of the general formula

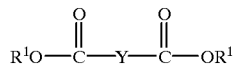

wherein Y is generally as defined above, and preferably a group of the formula —CH=CH—, and each $R^1$ is individually as defined above, preferably an aliphatic, alicyclic or aromatic group having up to 24 carbon atoms, more preferably an alkyl group of 1 to 8 carbon atoms, and especially an alkyl group of 1 to 4 carbon atoms;

with (2) an hydroxyalkylalkylene urea of the general formula

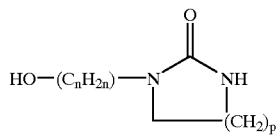

wherein n and p are as broadly defined above, with n preferably being 2 or 3 (and especially 2), and p preferably being 1, under conditions to replace, on at least a portion of the dicarboxylic acid diester, both $R^1$ groups with the hydroxyalkylalkylene urea. Preferably, the reaction is conducted in the presence of a transesterification catalyst and under other conditions generally as described above.

As indicated above, the product resulting from this reaction is actually a complex mixture of compounds, typically also with minor amounts of unreacted starting components. All products in the reaction mixture containing both ethylenic unsaturation and cyclic urea/ureido functionality have been found to impart wet adhesion properties to an ultimate polymer system. Among these products may be included generally predominant amounts the following "monomeric" diacid based compounds

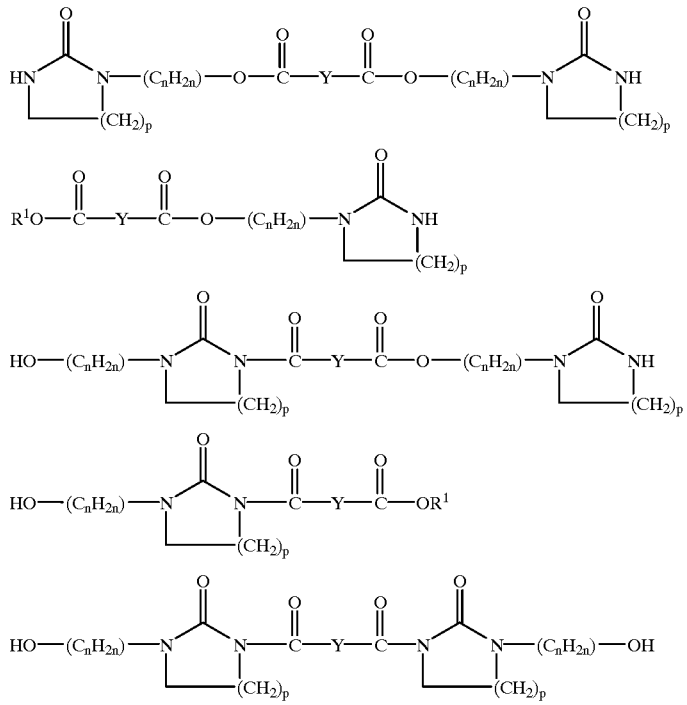

as well as lesser amounts of the following "oligomeric" diacid products

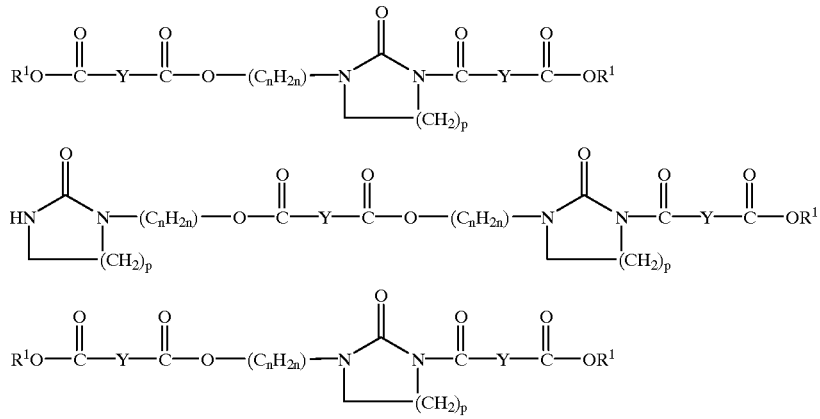

and other similar variations.

In fact, it is another aspect of the present invention to utilize this crude reaction mixture, in and of itself or further treated to remove a portion of the unreacted starting materials, as a wet adhesion promoting monomer composition, as further described below.

Uses of the Monomers of the Present Invention

The novel functional monomers represented by the Formula (I), and monomer mixtures described above, find use, for example in the preparation of polymers for adhesives, caulks, sealants, coatings, wood coatings, automotive coatings, binders, wet/dry strength resins for paper, paper coatings, textiles, lubricants, intermediates for surfactants, intercoat adhesion promoters, polymer compatibilizers, primers, surface modifiers, corrosion inhibitors and formaldehyde scavengers, pressure sensitive adhesives, nonwovens, can coatings, marine coatings, architectural coatings, and modifiers for cement, concrete, mortar and the like.

The novel monomers of the present invention are polymerizable or copolymerizable through the unsaturation in the compounds. They may be used as comonomers in monomeric systems for forming aqueous emulsion and other types of polymers, including in compositions comprising monomers such as acrylics, vinyls, vinyl aromatics, $\alpha,\beta$-unsaturated carboxylic acids and their esters, as well as other known specialty monomers. Examples of suitable acrylic monomers include methyl acrylate, ethyl acrylate, 2-ethylhexyl acrylate, methyl methacrylate, hydroxyalkyl acrylates, hydroxyalkyl methacrylates, butyl acrylate, hexyl acrylate, cyclohexyl acrylate, 2-hydroxyethyl methacrylate, 2-hydroxyethyl acrylate, 2-hydroxypropyl methacrylate, 2-hydroxypropyl acrylate, piperidinoethyl methacrylate, morpholinoethyl methacrylate, and the like.

Examples of suitable vinyl monomers include ethylene, propylene, butylene, isobutylene, hexene, vinyl acetate, vinyl esters of versatic acids (e.g., VEOVA-9 and VEOVA-10), vinyl chloride, acrylonitrile, acrylamide, methacrylamide, vinylidene chloride, oleic acid, linoleic acid, 1,3-butadiene, isoprene, norbornene, cyclopentadiene and the like.

Examples of useful unsaturated carboxylic acids include itaconic acid, citraconic acid, crotonic acid, mesaconic acid, maleic acid, fumaric acid, and the like; α,β-unsaturated dicarboxylic acid esters of the dicarboxylic acids described above including aromatic esters, cycloalkyl esters, alkyl esters, hydroxyalkyl esters, alkoxy alkyl esters, and the like.

Examples of suitable vinyl aromatic monomers, with which the present invention's monomers can be polymerized, include styrene, α-methylstyrene, vinyltoluene, ethylstyrene, isopropyistyrene, p-hydroxystyrene, p-acetoxystyrene, and p-chlorostyrene.

In particular, the monomers of this invention may be incorporated in effective amounts in polymer systems to enhance the adhesion/wet adhesion of paints made from the polymers.

The emulsion polymers used in formulating latex paints usually are all acrylic copolymers comprising alkyl esters of acrylic and methacrylic acid with minor amounts of acrylic and methacrylic acid, or they are vinyl/acrylic polymers comprising vinyl containing monomers or polymers in combination with softer acrylic monomers. The commonly used ethylenically unsaturated monomers in making acrylic paints are butyl acrylate, methyl methacrylate, ethyl acrylate and mixtures thereof. In acrylic paint compositions at least 50% of the polymer formed is comprised of an ester of acrylic or methacrylic acid. The vinyl-acrylic paints usually include ethylenically unsaturated monomers such as vinyl acetate and butyl acrylate or 2-ethylhexyl acrylate. In vinyl acrylic paint compositions, at least 50% of the polymer formed is comprised of vinyl acetate, with the remainder being selected from the esters of acrylic or methacrylic acid.

The monomers of this invention may be added to a monomer composition from which acrylic or vinyl acrylic polymers are formed in a concentration which may vary over a wide range. Preferably the concentration is at least sufficient to improve the wet adhesion of paints made from the polymer composition. Concentrations may range from about 0.05% to about 20%, by weight, based on the total weight of monomers. Preferably, the concentration is in the range of from about 0.1% to about 5.0%, and more preferably from about 0.5% to about 3.0%.

The monomer composition may be used in conjunction with other ingredients, such as various free radical catalysts to initiate polymerization, emulsifying agents to protect particles from agglomeration, and buffers to maintain a desired pH during polymerization, as is generally well-known to those of ordinary skill in the art of polymerization. For example, suitable free radical polymerization catalysts are the catalysts known to promote emulsion polymerization and include water-soluble oxidizing agents such as organic peroxides (e.g., t-butyl hydroperoxide, cumene hydroperoxide, etc.), inorganic oxidizing agents (e.g., hydrogen peroxide, potassium persulfate, sodium persulfate, ammonium persulfate, etc.) and those catalysts that are activated in the water phase by a water-soluble reducing agent. Such catalysts are employed in a catalytic amount sufficient to cause polymerization. Generally, a catalytic amount ranges from about 0.01 to 5.0 parts per hundred parts of monomer. As alternatives to heat and catalytic compounds to activate polymerization, other free radical producing means, such as exposure to activating radiations, can be employed.

Suitable emulsifying agents include anionic, cationic, and nonionic emulsifiers customarily used in emulsion polymerization. Usually, at least one anionic emulsifier is utilized and one or more nonionic emulsifiers may also be utilized. Representative anionic emulsifiers are the esters of sulfosuccinic acid, amides of sulfosuccinic acid, the alkyl aryl sulfonates, alkali metal alkyl sulfates, the sulfonated alkyl esters and fatty acid soaps. The emulsifying agents are employed in amounts to achieve adequate emulsification and to provide desired particle size and particle size distribution.

Examples of suitable buffers used to maintain a desired pH during polymerization include ingredients such as acids, salts, chain transfer agents and chelating agents. For example, if the polymerization constituents include a monoethylenically unsaturated carboxylic acid comonomer, polymerization under acidic conditions (pH 2–7, preferably 2–5) is preferred. In such instances, the aqueous medium can include those known weak acids and their salts that are commonly used to provide a buffered system at the desired pH range.

The manner of combining the polymerization ingredients can be various known monomer feed methods, such as, continuous monomer addition, incremental monomer addition, or addition in a single charge of the entire amount of monomers. The entire amount of the aqueous medium with polymerization additives can be present on the polymerization vessel before introduction of the monomer, or alternatively, the aqueous medium, or a portion of it, can be added continuously or incrementally during the course of the polymerization.

The polymerization of the monomer system which includes ethylenically unsaturated monomers and either one or more of the the novel monomers of the present invention can be accomplished by known procedures for polymerization in aqueous emulsions, as disclosed, for example, in U.S. Pat. No. 3,366,613, U.S. Pat. No. 4,104,220, U.S. Pat. No. 2,881,171, U.S. Pat. No. 4,219,452 and EP-A-0626672, which are incorporated by reference herein for all purposes as if fully set forth. Pre-polymer monomeric starting materials used to form polymeric pre-emulsion compositions using the monomers of the present invention are typically dissolved or suspended in the aqueous medium to a desired concentration. Preferably, the polymerization of the invention is performed at a concentration range of about 10 weight-% to about 70 weight-% of the monomers in the aqueous medium, although somewhat higher or lower concentrations may be employed in some cases.

By way of example, polymerization is initiated by heating the emulsified mixture with continued agitation to a temperature usually between about 50° C. to about 110° C., preferably between 60° C. to about 100° C. Heating of the emulsified mixture is also preferably conducted in an inert atmosphere (e.g., purging with nitrogen, argon, etc.). Polymerization is continued by maintaining the emulsified mixture at the desired temperature until conversion of the monomer or monomers to polymer has been reached.

Generally, depending upon the final application of the polymeric composition, the polymer may contain anywhere from about 0.05 weight-% to about 20.0 weight-% of the monomer of the present invention (based on the concentration of the monomer), preferably from about 0.1% to about 5.0 weight-% of the present monomer, and more preferably from about 0.5% to about 3.0 weight-% of the monomer of the present invention.

It is also within the scope of this invention to use blends of unmodified polymers with polymers produced using the monomers of the present invention. The unmodified polymers include acrylic, vinyl acrylic, styrene acrylic, styrene butadiene, styrene butadiene-acrylic, as well as polymers derived from esters of versatic acid (e.g., VEOVA-9 and VEOVA-1 0). The polymers modified with the inventive monomers may be utilized as a latex concentrate, with the polymer of the concentrate being prepared with higher amounts of the present monomers (for example, 20–50 % by weight based on the monomer mixture). These latex concentrates may be added to unmodified latices in amounts so as to result in an overall wet adhesion monomer content in the combined polymers within the ranges mentioned earlier.

In addition to making emulsion polymers, it is contemplated that preferably the monounsaturated monomers of the present invention be used to form solution copolymers. Polymerization towards the formulation of solution polymers may be completed under substantially similar circumstances as described above for emulsion polymerization except that the medium of polymerization in a solution polymerization reaction is organic instead of aqueous. Generally, the solution polymerization reaction is carried out with the monomers in solution in an inert organic solvent such as tetrahydrofuran, methyl ethyl ketone, acetone, ethyl acetate, or other suitable organic solvents such as hexane, heptane, octane, toluene, xylene and mixtures thereof. In the case of water-soluble monomers, inverse emulsions may also be prepared. Inverse emulsion being defined as a water-soluble polymer system dispersed in an organic solvent. Preferred solvents are non-toxic and odorless.

The invention will now be illustrated by the following examples. The examples are not intended to be limiting of the scope of the present invention. In conjunction with the general and detailed descriptions above, the examples provide further understanding of the present invention.

EXAMPLE 1

Reaction of HEEU with Dimethyl Maleate

Di-(β-(Ethyleneureido)ethyl)Maleate

Monomer M1

A mixture of 16.6 g (0.115 moles) of dimethyl maleate, 30 g (0.231 moles) of HEEU and 0.5 g of titanium isopropoxide was heated at 145° C. with stirring. Methanol formed from the reaction was distilled off. After about 5 hours, the theoretical amount of methanol (7.8 g) had been collected. The reaction mixture was cooled to room temperature and analyzed by NMR. Analysis indicated a mixture of cis- and trans-di-(β-(ethyleneureido)ethyl)maleate, cis- and trans-β-(ethyleneureido)ethyl methyl maleate and dimethyl maleate. $^1$H NMR (DMSO-$d_6$): δ 6.8–6.6 (m, 2 H), 6.5–6.4 (m, 2 H), 4.5–4.2 (m, 6 H), 3.6–3.2 (m, 12 H). LC-MS confirmed the presence of the above listed compounds.

EXAMPLE 2

Reaction of HEEU with Diethyl Maleate

Di-(β-(Ethyleneureido)ethyl)Maleate

Monomer M2

A mixture of 23.9 g (0.139 moles) of diethyl maleate, 36.08 g (0.278 moles) of HEEU and 0.7 g of Ti(OiPr)4 was heated at 145° C. Ethanol formed from the reaction was distilled off. After 4 hours the reaction mixture was cooled to room temperature. LC-MS analysis showed a mixture of cis- and trans-di-(β-(ethyleneureido)ethyl)maleate, cis- and trans-β-(ethyleneureido)ethyl ethyl maleate, diethyl maleate and minor amounts of other products containing both ethylenic unsatuation and HEEU derived groups.

EXAMPLE 3

Reaction of HEEU with HEEU Maleate

Di-(β-(Ethyleneureido)ethyl)Maleate

Monomer M3

A mixture of 1.43 g (0.011 moles) of HEEU and 2.3 g (0.01 moles) of HEEU maleate in 10 mL of $CH_2Cl_2$ was stirred at 0° C. Thionyl chloride (1.2 g, 0.01 moles) was added dropwise over 20 minutes. After addition was complete, the mixture was stirred for 12 hours at room temperature. The reaction mixture was filtered and evaporated to afford monomer mixture M3.

EXAMPLE 4

Reaction of HEEU with Fumaryl Chloride trans-Di-β-(Ethyleneureido)ethyl)Maleate

Monomer M4

A mixture of 2.6 g (0.02 moles) of HEEU and 1.53 g (0.01 moles) of fumaryl chloride in 10 mL of $CH_2Cl_2$ was stirred at 0° C. for 3 h, followed for 12 h at room temperature. The reaction mixture was filtered and evaporated to afford monomer mixture M4 containing higher amounts of oligomeric components.

EXAMPLE 5

Reaction of AEEU with AEEU Maleamide cis-Di-β-(Ethyleneureido)ethyl)Maleate

Monomer M5

A mixture of 1.42 g (0.011 moles) of AEEU and 2.27 g (0.01 moles) of HEEU Maleamide in 10 mL of $CH_2Cl_2$ was stirred at 0° C. Thionyl chloride (1.2 g, 0.01 moles) was added dropwise over 20 minutes. After addition was complete, the mixture was stirred for 12 hours at room temperature. The reaction mixture was filtered and evaporated to afford monomer M5.

EXAMPLE 6

Reaction of AEEU with Fumaryl Chloride trans-Di-β-(Ethyleneureido)ethyl)Fumaramide Monomer M6

A mixture 2.58 g (0.02 moles) of AEEU and 1.53 g (0.01 moles) of fumaryl chloride in 10 mL of $CH_2Cl_2$ was stirred at 0° C. for 3 hours, followed for 12 hours at room temperature. The reaction mixture was filtered and evaporated to afford monomer M6.

EXAMPLE 7

Reaction of Hydroxyethyl Methacrylate with HEEU Maleate

Monomer M7

A mixture of 2.3 g (0.01 moles) of HEEU maleate, 1.43 g (0.011 moles) of hydroxyethyl methacrylate, and 0.02 g of Ti(OiPr)$_4$ in 20 mL of toluene was heated to reflux. After 8 hours, the mixture was cooled to room temperature and 0.1 g of H$_2$O was added. The liquid phase was decanted and concentrated to afford a mixture by NMR and LC-MS analysis. The presence of an AB pattern at δ 4.4 indicated a HEMA maleate product. The product was confirmed by LC-MS identification (M+1=341).

EXAMPLE 8

Reaction of HEEU with HEMA Maleate

Monomer M8

A mixture of 6.2 g (0.027 moles) of HEMA maleate (made according to the procedure of U.S. Pat. No. 3,150,118), 3.9 g (0.03 moles) of HEEU, and 0.05 g of Ti(OiPr)$_4$ in 30 mL of toluene was heated to reflux. After 8 hours, the mixture was cooled to room temperature and 0.2 g of H$_2$O was added. The liquid phase was decanted and concentrated to afford a mixture containing monomer M35A in low yield by NMR and LC-MS analysis.

EXAMPLE 9

Reaction of HEMA with HEEU Maleate

Monomer M9

A mixture of 1.43 g (0.011 moles) of HEMA and 2.3 g (0.01 moles) of HEEU maleate in 10 mL of CH$_2$Cl$_2$ was stirred at room temperature. Thionyl chloride (1.2 g, 0.01 moles) was added dropwise over 20 minutes with control of the exotherm by a water bath. After addition was complete, the mixture was stirred for 1 hour at room temperature followed by refluxing for 12 hours. After cooling to room temperature, 2.1 g (0.021 moles) of N-methylmorpholine was added and the mixture stirred at room temperature for 12 hours. The reaction mixture was filtered and evaporated to afford monomer M9.

EXAMPLE 10

Reaction of HEMA with AEEU Maleate

Monomer M10

A mixture of 2.3 g (0.01 moles) of AEEU maleate (made according to the procedure of U.S. Pat. No. 2,980,652) and 1.43 g (0.011 moles) of HEMA in 10 mL of CH$_2$Cl$_2$ was stirred at room temperature. Thionyl chloride (1.2 g, 0.01 moles) was added dropwise over 20 minutes with control of the exotherm by a water bath. After addition was complete, the mixture was stirred for 1 hour at room temperature followed by refluxing for 12 hours. After cooling to room temperature, 2.1 g (0.021 moles) of N-methylmorpholine was added and the mixture stirred at room temperature for 12 hours. The reaction mixture was filtered and evaporated to afford monomer M10.

EXAMPLE 11

Reaction of HEEU with Maleamic Acid

Monomer M11

A mixture of 6.5 g of HEEU (0.05 moles), 5.75 g of maleamic acid (0.05 moles) and 50 mg of H$_2$SO$_4$ (0.0005 moles) in 20 mL of toluene was heated at 80° C. and partial vacuum to reflux the mixture. After 8 hours, the toluene was evaporated to afford a mixture of cis- and trans-HEEU maleamate.

EXAMPLES 12–17

These examples illustrate the utility of the monomers of the present invention in wet adhesion applications.

TEST PROCEDURE

A. Latex Preparation

The following general procedure was used in the synthesis of all acrylic latexes containing the monomers of the present invention. The wet adhesion monomer (WAM) used in the preparation of the acrylic latexes was either a monomer of the present invention or, alternatively, a commercially available wet adhesion monomer.

A 1 liter glass jacketed resin reactor with a bottom discharge valve was used. The reactor was equipped with thermometer, a circulating constant temperature heating bath, N$_2$ purge, a Teflon turbin agitator, a monomer emulsion feed pump calibrated for 4.59 grams/min and an initiator feed pump calibrated for 0.5 g/min.

The following charge is used:

|  | Wt. (g) |
| --- | --- |
| Reactor charge | |
| D.I. Water | 192.1 |
| Monomer Emulsion | |
| D.I. Water | 182.6 |
| Rhodacal ® DS4 (Surfactant) | 21.7 |
| Wet Adhesion Monomer (WAM) | 5.0 |
| Methylmethacrylate | 260.0 |
| Butylacrylate | 230.0 |
| Methacrylic acid | 2.7 |
| Initiator Solution | |
| Ammonium Persulfate* | 2.0 |
| D.I. Water | 98.0 |

*23% solution in water; product of Rhône-Poulenc Co.

The monomer emulsion was prepared by:
1. dissolving the surfactant in water;
2. if the WAM monomer was only water soluble, adding it to the water surfactant solution;
3. blending all the monomers together then, if the WAM monomer was soluble in the organic phase, dissolving it in the monomer blend; then
4. mixing the monomers with the water surfactant solution and keeping the mixture agitated to insure a homogeneous dispersion.

B. Polymerization Procedure

The reactor water was heated to 80° C. while the system was under a N$_2$ blanket. At 80° C., 25 grams of initiator solution and 14.2 grams of monomer emulsion were added. The temperature was held at ~80° C. for 15 minutes, then the the remainder of the monomer emulsion and initiator solutions were fed over a 2.5 hour period using the appropriate calibrated pumps. The polymerization temperature was maintained at 80±1° C. during the addition.

After completion of the monomer and initiator addition, the reaction mixture was heated to 85° C. for 30 minutes. The emulsion was then cooled to 23°–25° C. and the pH adjusted to 9.0±0.2 with 28% NH$_4$OH. The resulting emulsion was filtered through a cheesecloth paint filter.

The typical yield was ~955 grams, with a viscosity of 20–28 cps and solids of ~50%.

C. Wet Adhesion Test

The wet adhesion test utilized was a version of the scrub resistance test described in the ASTM procedure #D2486.

Using a 7 mil Dow bar, a film of Glidden Glid-Guard® 4554 gloss alkyd was cast on a Leneta scrub panel. The panels were aged for a minimum of 21 days, but not more than 6 weeks prior to use. The test paint was applied with a 7 mil Dow blade over the aged alkyd and air dried 4 hours, 24 hours and seven days. The test paint was cross-hatched in a 10×10 grid of 3 mm squares using a razor knife and template. The panels were then soaked in room temperature distilled water for 35 minutes, and any blistering or edge lift was recorded. If there was no blistering or edge lift from the water soak, the panel was placed on the scrub machine (described in ASTM procedure D2486). 25 ml of water was applied to the panel, and the scored area was scrubbed. During the scrubbing, more water was applied if the panel became dry. The percentage of the squares removed after 1000 cycles was recorded.

The physical properties of some of the latexes prepared using the monomers of the present invention are summarized in Table I, below. Included for comparison are latices containing no wet adhesion monomer, which control is indicated as sample "L-C," and commercially available SIPOMER® WAM II, indicated as sample "L-WII." The label M1 refers to monomers corresponding to the Examples described herein. All wet adhesion monomers were tested at 1 wt % level based on the final latex polymer.

TABLE I

| | | | | Physical Properties | |
|---|---|---|---|---|---|
| Example | Sample | Monomer | pH | % Solids | Particle Size (Microns) |
| 12 | L-C | None | 9.02 | 49.3 | 0.21–0.25 |
| 13 | L-WII | SIPOMER® WAM II | 9.03 | 51.2 | 0.21–0.25 |
| 14 | L-M1 | M1 | 9.02 | 50.6 | 0.21–0.25 |
| 15 | L-M2 | M2 | 90.1 | 49.7 | 0.21–0.25 |

The above latices were formulated into semigloss latex exterior house paint for measurement of wet adhesion properties. The recipe used for the paint formulation is shown below in Table II. The results of the wet adhesion properties of the above-described monomers and other monomers of the present invention are shown in Table IV, below.

TABLE II

| Paint | Wt. |
|---|---|
| Water | 166.6 |
| Polyphobe 102 | 8.8 |
| Amp 95 | 3.0 |
| Nuosept 95 | 2.3 |
| Propylene glycol | 60.5 |
| Colloid 286 | 7.4 |
| Colloid 653 | 1.9 |
| Triton N-57 | 2.1 |
| Tronox CR-828 | 250.0 |
| Attagel 50 | 2.0 |
| Grind | |
| Water | 73.7 |
| Polyphobe 102 | 13.2 |
| Water | 12.5 |
| Latex | 420.8 |
| UCAR Filmer IBT | 10.5 |
| Colloid 653 | 2.8 |
| Polyphase AF-1 | 7.3 |
| Triton GR-7M | 1.1 |
| Totals | 1052.5 |

Table III identifies the various ingredients used in the paint formulation. The ingredients were added in the order listed to a high speed paint disperser.

TABLE III

EXTERIOR TRIM HOUSE PAINT

| PAINT | DESCRIPTION |
|---|---|
| Added in order to high speed disperser | |
| Water | |
| Polyphobe 102 | Rheology Modifier |
| Amp 95 | Amine, 2-Amino-2-Methyl Propanol |
| Nuosept 95 | In can preservative, bicyclic oxazolidines |
| Propylene Glycol | Open Time |
| Colloid 280 | Dispersant, Ammonium Polyacrylic Copolymer Solution |
| Colloid 653 | Defoamer, Hydrophobic Silica Defoamer |
| Triton N-67 | Nonionic Surfactant |
| Tronox CR-828 | Titanium Dioxide |
| Attagel 50 | Attapulgite Clay |
| Grind 20 minutes | |
| Add the following in order | |
| Water | |
| Polyphobe 102 | Rheology Modifier |
| Water | |
| Latex | |
| UCAR Filmer IBT | Coalescent Solvent, Ester Alcohol |
| Colloid 653 | Defoamer, Hydrophobic Silica Defoamer |
| Polyphase AF-1 | Mildewcide, 3 Iodo-2Propynyl Butyl Carbamate |
| Triton GR-7M | Anionic Surfactant, Dioctyl Sodium Sulfosuccinate |

The wet adhesion test results obtained with latex paints containing the wet adhesion monomers of the present invention are shown in Table IV. Included for comparison are the paints containing no wet adhesion monomer ("P-L-O") and commercially available wet adhesion monomer SIPOMER® WAM II ("P-L-WII"). As stated above, the label M1 refers to monomers corresponding to the Examples described herein.

TABLE IV

WET ADHESION RESULT

| Paint Formulation | 4-Hr Wet Adhesion Glidden 4554 Med. Green % Removed in 1000 cycles | 24-Hr Wet Adhesion Glidden 4554 Med. Green % Removed in 1000 cycles | 7-Day Wet Adhesion Glidden 4554 Med. Green % Removed in 1000 cycles |
|---|---|---|---|
| Example 12 P-L-O No Wet Adhesion Monomer | 100 | 100 | 100 |
| Example 13 P-L-WII 1% SIPOMER WAM II | 0 | 0 | 0 |

TABLE IV-continued

| | WET ADHESION RESULT | | |
|---|---|---|---|
| Paint Formulation | 4-Hr Wet Adhesion Glidden 4554 Med. Green % Removed in 1000 cycles | 24-Hr Wet Adhesion Glidden 4554 Med. Green % Removed in 1000 cycles | 7-Day Wet Adhesion Glidden 4554 Med. Green % Removed in 1000 cycles |
| Example 14 P-L-M1 1% Monomer M1 | 0 | 0 | 0 |
| Example 15 P-L-M2 1% Monomer M2 | 0 | 0 | 0 |

The results in Table IV show that without the addition of the wet adhesion monomer, the paint films are completely removed regardless of the drying period and that the monomers of the present invention are at least equivalent to the commercially used monomer SIPOMER® WAM II at the levels tested.

EXAMPLE 16

Following the test procedure of Example 14, when M1 was replaced with M5, and tested in accordance therewith, substantially equivalent results were obtained.

EXAMPLE 17

Following the test procedure of Example 14, when M1 was replaced with M6, and tested in accordance therewith, substantially equivalent results were obtained.

Although the present invention is described with reference to certain preferred embodiments, it is apparent that variations or modifications thereof may be made by those skilled in the art without departing from the scope of this invention as defined by the appended claims.

What is claimed is:

1. A compound represented by the formula (I)

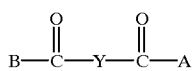

(I)

wherein Y is

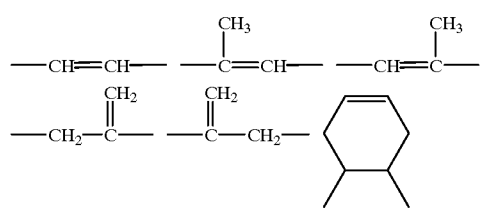

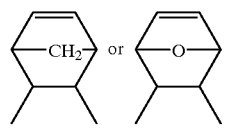

wherein A is

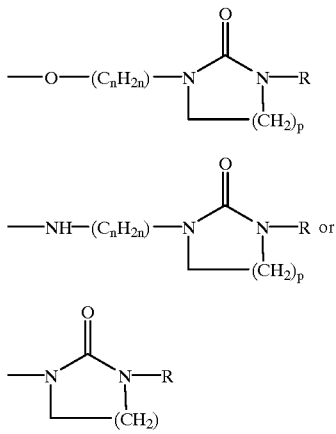

wherein B is

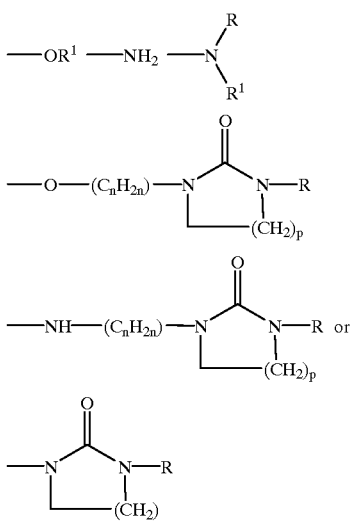

wherein each R is individually

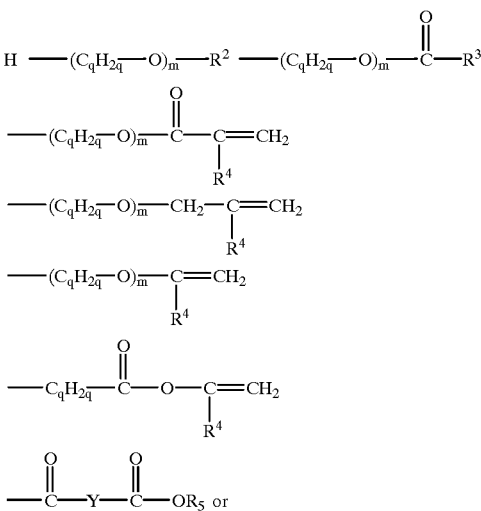

-continued

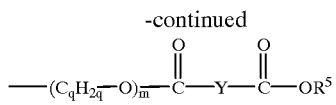

wherein each $R^1$ is individually an aliphatic, alicyclic or aromatic moiety having up to 24 carbon atoms

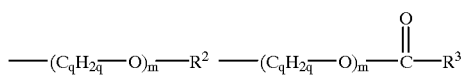
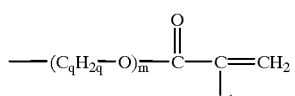
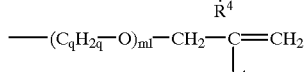
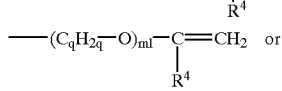
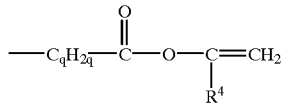

wherein each $R^2$ is individually hydrogen or an aliphatic, alicyclic or aromatic moiety having up to 24 carbon atoms wherein each $R^3$ is individually an aliphatic, alicyclic or aromatic moiety having up to 24 carbon atoms wherein each $R^4$ is individually hydrogen or a methyl group wherein each $R^5$ is individually hydrogen or an aliphatic, alicyclic or aromatic moiety having up to 24 carbon atoms wherein m is an integer of from 1 to 4 wherein m1 is 0 or an integer of from 1 to 4 wherein n is an integer of from 1 to 8 wherein p is 1 or 2, and wherein q is an integer of from 2 to 4, with the provisos that:

(1) when A is

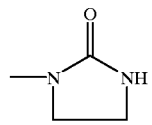

and B is —$OR^1$, then $R^1$ is

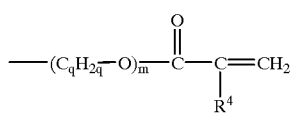
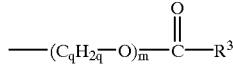

-continued

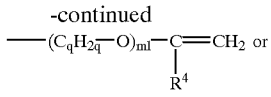
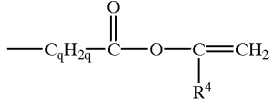

(2) when A is

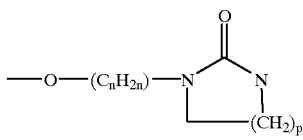

and B is —$OR^1$, then $R^1$ is an aliphatic, alicyclic or aromatic moiety having up to 24 carbon atoms

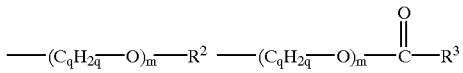
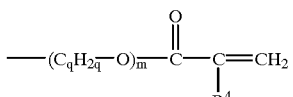
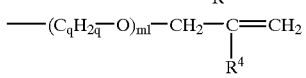
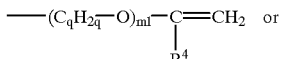
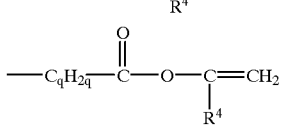

wherein $R^2$ is an aliphatic, alicyclic or aromatic moiety having up to 24 carbon atoms; and (3) when A is

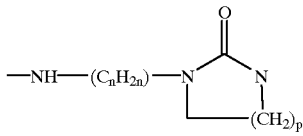

and B is —$OR^1$, then $R^1$ is

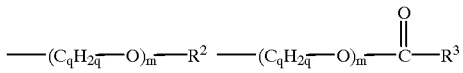
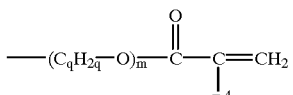
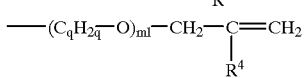

-continued

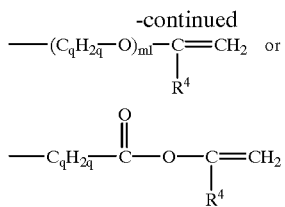

wherein $R^2$ is an aliphatic, alicyclic or aromatic moiety having up to 24 carbon atoms.

2. A monomer composition prepared by reacting: (1) an unsaturated dicarboxylic acid diester of the formula

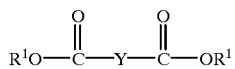

wherein Y is

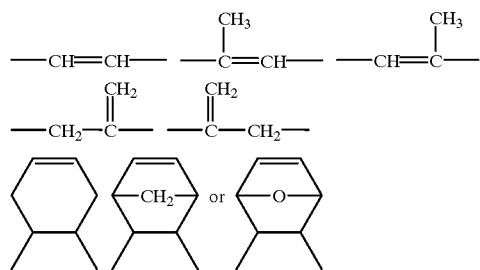

wherein each $R^1$ is individually an aliphatic, alicyclic or aromatic moiety having up to 24 carbon atoms

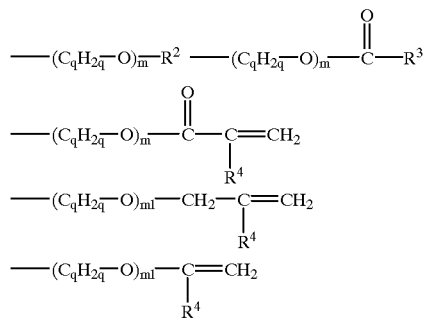

or

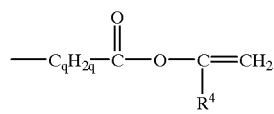

wherein each $R^2$ is individually hydrogen or an aliphatic, alicyclic or aromatic moiety having up to 24 carbon atoms
wherein each $R^3$ is individually an aliphatic, alicyclic or aromatic moiety having up to 24 carbon atoms
wherein each $R^4$ is individually hydrogen or a methyl group
wherein m is an integer of from 1 to 4
wherein m1 is 0 or an integer of from 1 to 4
wherein q is an integer of from 2 to 4;

with (2) an hydroxyalkylalkylene urea of the formula

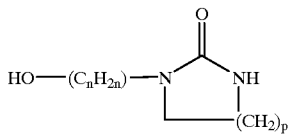

wherein n is an integer of from 1 to 8, and
wherein p is 1 or 2;
in the temperature range of 110° C.–150° C. and in the presence of a transesterification catalyst wherein at least one —$OR^1$ group of the unsaturated dicarboxylic acid diester is replaced by a residue of the hydroxyalkylene urea selected from the group consisting of:

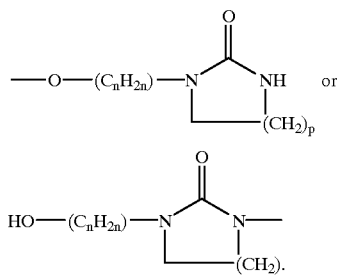

3. The compound of claim 1, wherein each $R^1$ is individually
an aliphatic, alicyclic or aromatic moiety having up to 24 carbon atoms

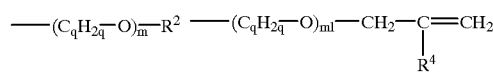

or

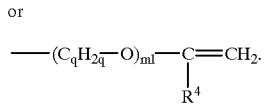

4. The compound of claim 2, wherein each $R^1$ is individually
an aliphatic, alicyclic or aromatic moiety having up to 24 carbon atoms

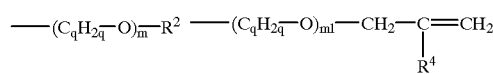

or

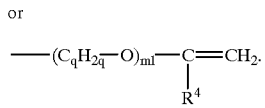

5. The compound of claim 1, wherein A and B are each

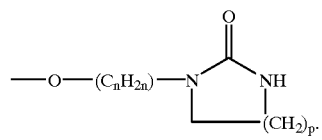

6. The compound of claim 1, wherein A is

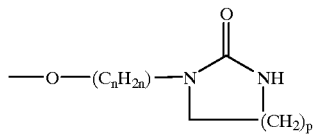

and B is —OR¹.

7. The compound of claim 1, wherein A is

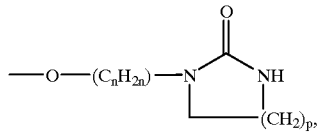

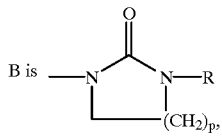

R is —$(C_qH_{2q}-O)_m$—R², m is 1, and R² is H.

8. The compound of claim 1, wherein B is —OR¹, A is

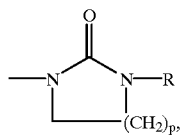

R is —$(C_qH_{2q}-O)_m$—R², m is 1, and R² is H.

9. The compound of claim 1, wherein A and B are each

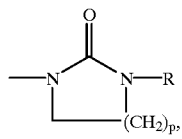

R is —$(C_qH_{2q}-O)_m$—R², m is 1, and R² is H.

10. The compound of claim 1, wherein Y is

—CH=CH—, and A and B are each

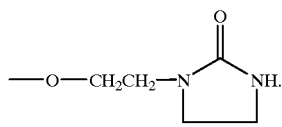

11. The compound of claim 1, wherein Y is

—CH=CH—,

A is

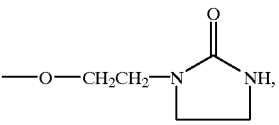

and B is

—OCH₃.

12. The compound of claim 1, wherein Y is

—CH=CH—,

A is

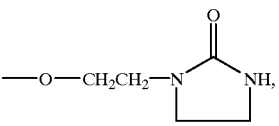

and B is

—OC₂H₅.

13. The compound of claim 1, wherein Y is

—CH=CH—,

A is

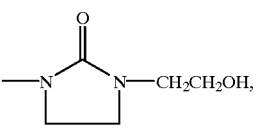

and B is —OCH₃.

14. The compound of claim 1, wherein Y is

—CH=CH—,

A is

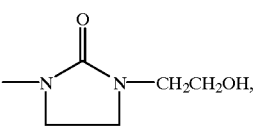

and B is —OC₂H₅.

15. The compound of claim 1, wherein Y is

—CH=CH—,

A is

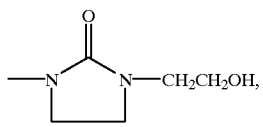

and B is

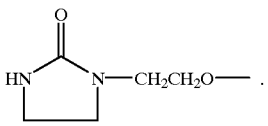

16. The compound of claim 1, wherein Y is

—CH=CH—, and A and B are each

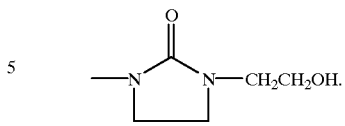

17. The monomer composition of claim 2, wherein the unsaturated dicarboxylic acid diester is dimethyl maleate, and the hydroxyalkylalkylene urea is hydroxyethylethylene urea.

18. The monomer composition of claim 2, wherein the unsaturated dicarboxylic acid diester is diethyl maleate, and the hydroxyalkylalkylene urea is hydroxyethylethylene urea.

19. The monomer composition of claim 2, wherein the unsaturated dicarboxylic acid diester is dimethyl fumarate, and the hydroxyalkylalkylene urea is hydroxyethylethylene urea.

20. The monomer composition of claim 2, wherein the unsaturated dicarboxylic acid diester is diethyl fumarate, and the hydroxyalkylalkylene urea is hydroxyethylethylene urea.

* * * * *

UNITED STATES PATENT AND TRADEMARK OFFICE
CERTIFICATE OF CORRECTION

PATENT NO.   : 6,166,220
DATED        : December 26, 2000
INVENTOR(S)  : Balwant Singh, Roland Ralph DiLeone, Laurence Wu-Kwang Chang It is certified that error appears in the above-identified patent and that said Letters Patent is hereby corrected as shown below:

In the Structure, Formula (I), Column 20,
Lines 14 to 19; lines 38 to 42 should appear as follows:

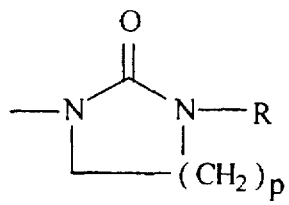

The next set of errors is not the fault of the Applicants.
In the Structure, Formula (I), Column 22,
Lines 12 to 17; column 22 lines 48 to 52 should appear as follows:

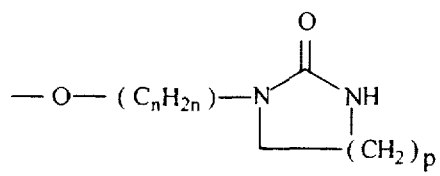

Signed and Sealed this

Twenty-third Day of October, 2001

*Attest:*

NICHOLAS P. GODICI
*Attesting Officer*     *Acting Director of the United States Patent and Trademark Office*